United States Patent [19]

Shiozawa et al.

[11] Patent Number: 4,841,051
[45] Date of Patent: Jun. 20, 1989

[54] PHENYLPIPERAZINE DERIVATIVES

[75] Inventors: Akira Shiozawa, Saitama; Yuh-Ichiro Ichikawa, Tokyo; Takashi Takahira, Saitama, all of Japan

[73] Assignee: Nippon Kayaku Kabushiki Kaisha, Tokyo, Japan

[21] Appl. No.: 936,270

[22] Filed: Dec. 1, 1986

[30] Foreign Application Priority Data

Dec. 10, 1985 [JP] Japan .................................. 60-277412

[51] Int. Cl.$^4$ ............................................. C07D 403/06
[52] U.S. Cl. ...................................... 544/287; 544/279
[58] Field of Search ............................................ 544/287

[56] References Cited

U.S. PATENT DOCUMENTS

| | | | |
|---|---|---|---|
| 3,231,572 | 1/1986 | Hayao | 260/256.4 |
| 4,578,465 | 3/1986 | Nagano et al. | 544/285 |
| 4,608,375 | 8/1986 | Ueda et al. | 514/218 |

FOREIGN PATENT DOCUMENTS

| | | |
|---|---|---|
| 161498 | 11/1985 | European Pat. Off. |
| 3326118 | 2/1984 | Fed. Rep. of Germany |

OTHER PUBLICATIONS

Mukerji et al., "Indian Journal of Pharm. Sci.", vol. 40(2), 1978, pp. 44–47.

*Primary Examiner*—Glennon H. Hollrah
*Assistant Examiner*—James H. Turnipseed
*Attorney, Agent, or Firm*—Henry C. Nields

[57] ABSTRACT

The present invention relates to a phenylpiperazine derivative represented by the general formula:

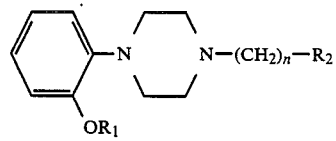

wherein $R_1$ stands for a lower alkyl group; $R_2$ stands for a group represented by the general formula:

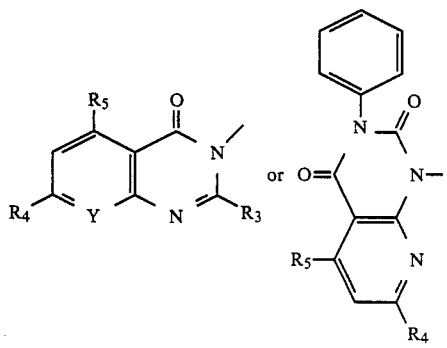

(wherein $R_3$, $R_4$ and $R_5$ each stand for a hydrogen atom or a lower alkyl group and Y stands for CH or N); and n stands for an integer of 1 to 6, and pharmaceutically acceptable acid addition salts thereof, which exhibit an $\alpha_1$-blocking activity and therefore are expected to be useful as a hypotensive drug.

3 Claims, No Drawings

PHENYLPIPERAZINE DERIVATIVES

FIELD OF THE INVENTION

The present invention relates to a novel phenylpiperazine derivative which can block α-receptors, particularly α₁-receptor, to thereby exhibit a hypotensive activity.

BACKGROUND OF THE INVENTION

A hypotensive agent with α₁-blocking activity is known, for example, 1-(4-amino-6,7-dimethoxy-2-quinazolinyl)-4-(2-furanylcarbonyl)piperazine, generally called prazosin (see U.S. Pat. No. 3,511,836).

Since, however, medicine is a foreign substance to a living body, the dose thereof is preferably as small as possible, so that development of a new medicine which can exhibit a stronger activity has been desired.

SUMMARY OF THE INVENTION

The inventors of the present invention have found as the result of extensive studies that a phenylpiperazine derivative represented by the general formula:

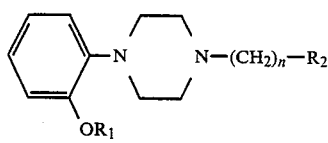

(I)

wherein $R_1$ stands for a lower alkyl group; $R_2$ stands for a group represented by the formula:

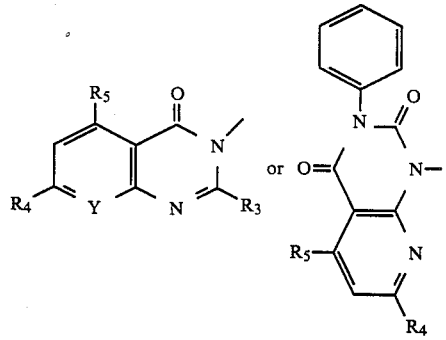

(wherein $R_3$, $R_4$ and $R_5$ each stand for a hydrogen atom or a lower alkyl group and Y stands for CH or N); an n stands for an integer of 1 to 6, exhibits a strong α₁-blocking activity to thereby exhibit a hypotensive activity.

The present invention has been accomplished on the basis of this finding.

Examples of the lower alkyl group of $R_1$, $R_3$, $R_4$ or $R_5$ of the above formulas include ones having 1 to 4 carbon atoms, such as methyl, ethyl, propyl and butyl groups.

Representative examples of the compound according to the present invention are shown in the following Tables.

TABLE 1

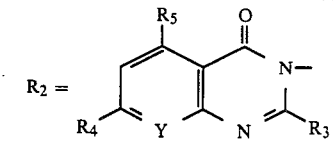

$R_2 =$

| Compound No. | $R_1$ | Y | n | $R_3$ | $R_4$ | $R_5$ |
|---|---|---|---|---|---|---|
| 1 | $C_2H_5$ | CH | 2 | H | H | H |
| 2 | $C_2H_5$ | CH | 3 | H | H | H |
| 3 | $C_2H_5$ | CH | 2 | $CH_3$ | H | H |
| 4 | $C_2H_5$ | CH | 3 | $CH_3$ | H | H |
| 5 | $C_2H_5$ | CH | 4 | H | H | H |
| 6 | $C_2H_5$ | N | 3 | $CH_3$ | $CH_3$ | $CH_3$ |
| 7 | $C_2H_5$ | N | 4 | $CH_3$ | $CH_3$ | $CH_3$ |
| 8 | $C_2H_5$ | N | 2 | $CH_3$ | $CH_3$ | $CH_3$ |
| 9 | $C_2H_5$ | N | 2 | $CH_3$ | $CH_3$ | $CH_3$ |

TABLE 2

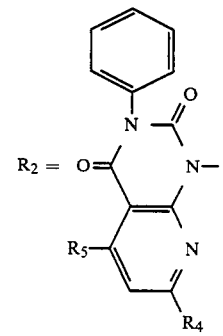

$R_2 =$

| Compound No. | $R_1$ | n | $R_4$ | $R_5$ |
|---|---|---|---|---|
| 10 | $C_2H_5$ | 2 | $CH_3$ | $CH_3$ |
| 11 | $C_2H_5$ | 4 | $CH_3$ | $CH_3$ |

Among them, preferred compounds are ones of Nos. 1, 3, 5 and 6.

The compounds represented by the general formula (I) can be prepared by a process selected from among the following processes.

$$R_2-H + X-(CH_2)_n-X \longrightarrow R_2-(CH_2)_n-X +$$ (1)
(II)　　　(III)　　　　　　　(IV)

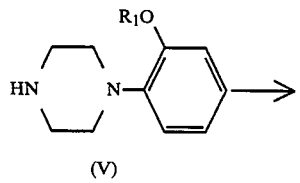

(V)

(I)

wherein $R_1$, $R_2$ and n are as defined above and X stands for a halogen atom.

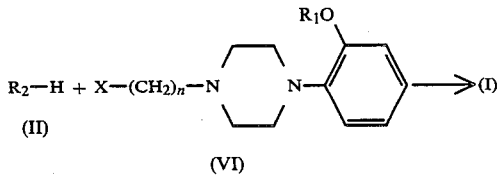

wherein $R_1$, $R_2$, n and X are as defined above.

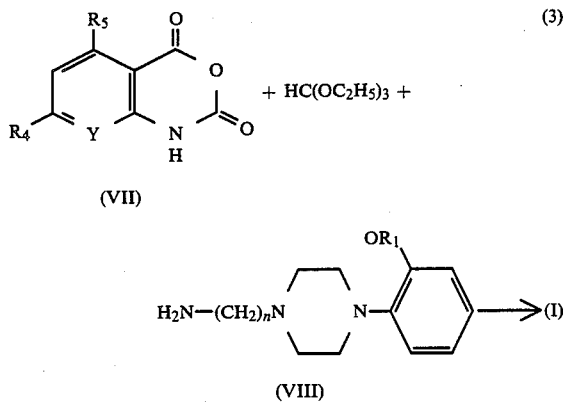

wherein $R_1$, $R_4$, $R_5$, Y and n are as defined above.

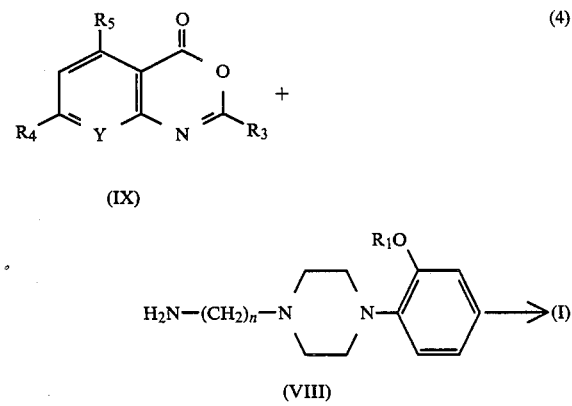

wherein $R_1$, $R_3$, $R_4$, $R_5$, Y and n are as defined above.

According to the process (1), a compound represented by the general formula (II) is reacted with a dihalogenoalkane derivative represented by the general formula (III) in the presence of a strong base catalyst such as sodium hydride or sodium amide in an inert solvent such as anhydrous dimethylformamide or anhydrous tetrahydrofuran at a temperature from a room temperature to the boiling point of the solvent to give a compound represented by the general formula (IV). The obtained (IV) compound is reacted with a piperazine derivative represented by the general formula (V) in the presence of a weak base catalyst such as triethylamine in an alcoholic solvent such as ethanol or propanol to give an objective compound of the general formula (I) according to the present invention.

Examples of the compound represented by the general formula (II) to be used in this process include 5,7-dimethylpyrido[2,3-d]pyrimidin-4(3H)-one, 2,5,7-trimethylpyrido[2,3-d]pyrimidin-4(3H)-one, 3-phenyl-5,7-dimethylpyrido[2,3-d]pyrimidin-4(3H)-one and, 2,5,7-triethylpyrido[2,3-d]pyrimidin-4(3H)-one.

Examples of the compound represented by the general formula (III) include 1,2-dibromoethane and 1,3-dibromopropane.

Examples of the compound represented by the general formula (V) include 4-(2-methoxyphenyl)-1-piperazine and 4-(2-ethoxyphenyl)-1-piperazine.

According to the process (2), a compound represented by the general formula (II) is reacted with a compound represented by the general formula (VI) in the presence of a base catalyst such as anhydrous potassium carbonate in an inert solvent such as dimethylformamide at a temperature of room temperature to 100° C. for several hours to give an objective compound represented by the general formula (I). Examples of the compound represented by the general formula (II) to be used in this process are the same as those to be used in the process (1), while examples of the compound represented by the general formula (VI) include 4-(2-chloroethyl)-1-(2-ethoxyphenyl)piperazine and 4-(2-chloropropyl)-1-(2-methoxyphenyl) piperazine.

According to the process (3), a compound represented by the general formula (VII) is reacted with ethyl orthoformate and an amine represented by the general formula (VIII) without any solvent or in an inert solvent such as toluene or dimethylformamide at a temperature of 100° to 150° C. for several hours to give an objective compound represented by the general formula (I).

Examples of the compound represented by the general formula (VII) to be used in this process include 2H-3,1-benzoxazine-2,4(1H)-dione and 2H-pyrido[2,3-d][1,3]oxazine-2,4-(1H)-dione, while examples of the amine represented by the general formula (VIII) include 1-(2-aminoethyl)-4-(2-methoxyphenyl)piperazine, 1-(2-aminoethyl)-4-(2-ethoxyphenyl)piperazine, 1-(3-aminopropyl)-4-(2-methoxyphenyl)piperazine, 1-(3-aminopropyl)-4-(2-ethoxyphenyl)piperazine, 1-(4-aminobutyl)-4-(2-ethoxyphenyl)piperazine and 1-(2-aminoethyl)-4-(2-butoxyphenyl)piperazine.

According to the process (4), an oxazine derivative represented by the general formula (IX) is reacted with an amine represented by the general formula (VIII) without any solvent or in an inert solvent for several hours under heating to give an objective compound (I). When no solvent is used, the reaction temperature is 100° to 150° C., while when an inert solvent is used, it is near the boiling point of the solvent.

Examples of the compound represented by the general formula (IX) include 2-methyl-4H-3,1-benzoxazin-4-one, 2-ethyl-4H-3,1-benzoxazin-4-one, 2-propyl-4H-3,1-benzoxazin-4-one, 2-butyl-3,1-benzoxazin-4-one, 2,5,7-trimethyl-4H-pyrido-[2,3-d][1,3]oxazin-4-one and 5,7-dimethyl-2-ethyl-4H-pyrido[2,3-d][1,3]oxazin-4-one.

Examples of the compound represented by the general formula (VIII) are the same as those above-mentioned.

The compounds obtained by these processes can be converted into pharmaceutically acceptable addition salts thereof with an inorganic acid such as hydrochloric, sulfuric or phosphoric acid or an organic acid such as maleic or fumaric acid.

[Pharmacological Activity]

Pharmacological activity of the compound thus obtained will be described.

(1) Action on isolated vas deferens of a rat

The vas deferens was isolated from SD male rats and cut into strips about 20 mm long. The both ends of the strip were bounded with two threads respectively. The thread attached to one end of the strips was fixed in a 10-ml organ bath and the thread attached to other end was connected to an isotonic transducer. The bath was filled with Tyrode's solution of 32° C. comprising a solution of 8.0 g of NaCl, 0.2 g of KCl, 0.2 g of $CaCl_2$, 0.1 g of $MgCl_2$, 0.05 g of $NaH_2PO_4$, 1.0 g of $NaHCO_3$ and 1.0 g of glucose in 1 l of deionized water. A gas mixture comprising 95% of oxygen and 5% of carbon dioxide was bubbled into the bath. Resting tension of 0.5 g was loaded. Noradrenaline was treated accumulatively in the bath to obtain a consistent dose-response curve. After the pretreatment of the preparation with a sample compound for 3 minutes, another dose-response curve of noradrenaline was obtained to determine the activities of the compound. The strength of antagonism against noradrenaline was determined from these dose-response curves in terms of $pA_2$ value. The results are shown in Table 3.

(2) Hypotensive activity

The experiment was carried out using an SHR or SD male rat under anesthesia. The blood pressure was measured by inserting a polyethylene tube (a product of Clay Adams Co., Ltd.: PE-50) into its carotid arteries and using a pressure transducer (a product of Century Technology Company: CP-01) and continuously recorded on a recorder (a product of Nippon Koden Co., Ltd.). Sample compounds were each injected by a polyethylene tube (a product of Clay Adams Co., Ltd.: PE-10) inserted into the femoral vein of the rat in an amount of 3 μg/kg for an SHR rat or 10 μg/kg for an SD rat to examine the maximum hypotensive effect on systolic pressure. The results are shown in Table 3.

(3) Acute toxicity

The acute toxicity due to intraperitoneal administration of a sample compound was examined by using ICR male mice (CRJ-ICR: weight of 29.5 to 52.3 g). Each sample compound was administered to from ten to thirty mice. The mice were observed until the symptom got well again. The $LD_{50}$ values were determined by the up-and-down method or by van der Welden method. The results are shown in Table 3.

TABLE 3

| Compound No. | (1) $pA_2$ | (2) SHR rat | (2) SD rat | $LD_{50}$ |
|---|---|---|---|---|
| 1 | 9.3 | *+++ | — | 400 |
| 3 | 8.5 | +++ | — | 119 |
| 4 | 8.0 | ++ | — | 152 |
| 5 | 9.4 | +++ | 57.5 mmHg | 150 |
| 6 | 8.6 | ++ | — | 128 |
| 7 | 8.3 | ++ | — | 137 |
| 8 | 8.2 | ++ | — | 207 |
| 10 | 8.1 | ++ | — | 328 |

*+ pressure drop of 0 to 10 mmHg
++ pressure drop of 11 to 20 mmHg
+++ pressure drop of 21 to 30 mmHg

(4) $\alpha_1$-blocking activity

The blood pressure (a) of an SD male rat of 7 to 8 weeks of age was measured and 2 μg/kg of phenylephrine was administered to the rat by intravenous injection. Then the maximum response of blood pressure (b) was measured. 10 μg/kg of a sample compound was administered to the rats, followed by the intravenous injection of 2 μg/kg of phenylephrine. Then, the maximum response of blood pressure (c) was measured. The depression (d) of blood pressure increased due to phenylephrine was calculated by the following equation:

$$(d) = \frac{b-c}{b-a} \times 100\%$$

The results are shown in Table 4.

| Compound No. | Percentage of inhibition of blood pressure increase (%) |
|---|---|
| 5 | 89.6 |

The animal was anesthetized by intraperitoneal administration of 40 mg/kg of nembutal and the anesthetic depth was kept by intravenous drip infusion of 15 mg/kg/hr of pentobarbital sodium. The blood pressure was measured by inserting a polyethylene tube (a product of Clay Adams: PE-50) and using a transducer (a product of Century Technology Company: CP-01) and continuously recorded on a pen oscillograph (a product of Nippon Koden Co., Ltd. WI-6416). Each sample compound was injected by a polyethylene tube (a product of Clay Adams Co., Ltd.: PE-10) inserted into the femoral vein.

As described above, the compound of the present invention exhibits strong $\alpha_1$-blocking and hypotensive activities and the toxicity thereof is low. Therefore, the compound is expected to be effective in the treatment of hypertension and the like.

When the compound of the present invention is used as a hypotensive drug, the dose varies depending upon the symptom or age of a patient or the method of administration and is generally 0.1 to 10 mg/kg/day.

The compound of the present invention can be administered per se or parenterally in the form of tablet, granule, fine granule, powder, capsule, injection or suppositories, which can be prepared by mixing said compound with various carriers.

Process for preparing the compound of the present invention will be described by the following Examples.

EXAMPLE 1

(1)
3-[2-[4-(2-Ethoxyphenyl)-1-piperazinyl]-ethyl]-4(3H)-quinazolone (Compound No. 1) difumarate A mixture comprising of 1.63 g 2H-3,1-benzoxazine-2,4-(1H)-dione, 1.78 g of ethyl orthoformate and 2.49 g of 4-(2-ethoxyphenyl)-1-(2-aminoethyl)piperazine was heated on a boiling water bath for about 10 minutes and further heated on an oil bath of 120° to 130° C. for about 2 hours. After the completion of the reaction, the reaction mixture was concentrated under a reduced pressure. The obtained residue was columnchromatographed over silica gel column and eluted with an ethyl acetate-triethylamine solvent (30:1) to give 3.75 g of 3-[2-[4-(2-ethoxyphenyl)-1-piperazinyl]-ethyl]-4(3H)-quinazolone as an oil (yield: 99.2%).

Mass m/z(relative intensity): 378 (M+, 21.4), 233 (24.3), 219 (100.0), 205 (22.3), 177 (26.2)

This oil was dissolved in a small amount of acetone and the obtained solution was added to a saturated solution of 2.30 g of fumaric acid in acetone. The precipitated crude crystals were recrystallized from ethanol to give 4.2 g of a pure product.

dimfumarate m.p.: 169 to 171° C.
NMR δ (d₆—DMSO): 1.30(3H, t, J = 7.0 HZ; —OCH₂C<u>H</u>₃)

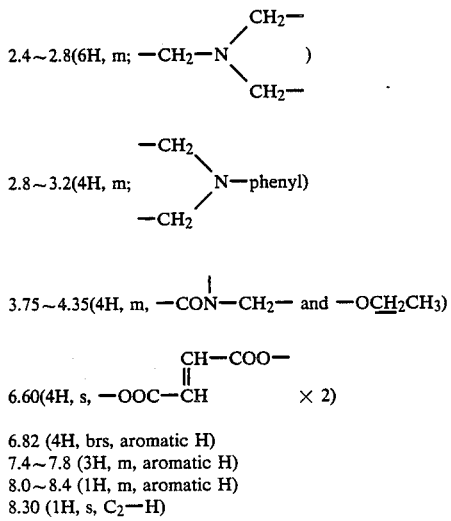

2.4~2.8(6H, m; —CH₂—N(CH₂—/CH₂—))

2.8~3.2(4H, m; —CH₂\N—phenyl / —CH₂)

3.75~4.35(4H, m, —CON—CH₂— and —OC<u>H</u>₂CH₃)

6.60(4H, s, —OOC—CH=CH—COO— × 2)

6.82 (4H, brs, aromatic H)
7.4~7.8 (3H, m, aromatic H)
8.0~8.4 (1H, m, aromatic H)
8.30 (1H, s, C₂—H)

The following compound was prepared in a similar manner as above.

| Compound No. | Mass m/z (relative intensity): | Monofumarate mp. |
|---|---|---|
| 2 | 392 (M⁺, 100), 246 (15.2), 232 (23.8), 218 (42.9), 204 (21.4) | 176~178° C. (EtOH) |

EXAMPLE 2

2,5,7-Trimethyl-3-[3-[4-(2-ethoxyphenyl)-1-piperazinyl]-propyl]pyrido[2,3-d]pyrimidin-4(3H)-one (Compound No. 6) monofumarate A mixture comprising of 3.32 g 2-amino-4,5-dimethylnicotinic acid, 19 ml of acetic anhydride and 100 ml of pyridine was heated at 145° C. for 2 hours. After the completion of the reaction, the reaction mixture was concentrated under a reduced pressure to give crude 2,5,7-trimethylpyrido-[2,3-d][3,1]oxazin-4-one. The crude product was mixed with 5.27 g of 4-(2-ethoxyphenyl)-1-(3-aminopropyl)piperazine and 75 ml of pyridine. The obtained mixture was heated at 135° C. for 2 hours. After the completion of the reaction, the reaction mixture was concentrated under a reduced pressure. An aqueous dilute solution of caustic soda was added to the obtained residue. The resulting mixture was extracted with toluene. The obtained organic layer was dried over anhydrous potassium carbonate and distilled under a reduced pressure to remove the solvent. The obtained residue was columnchromatographed over silica gel and eluted with an ethyl acetate-triethylamine mixture (5:1) to obtain 6.3 g of an oil. This oil was crystallized by the addition of isopropyl ether and recrystallized from isopropyl ether. 5.10 g of a colorless prismatic crystal was obtained (yield: 58.6%).

| mp. 105 ~ 107° C. |
|---|
| Mass m/z (relative intensity): 436 (M⁺ + 1, 30.3), 345 (M⁺, 100), 219 (33.7), 203 (37.3), 190 (39.6), 134 (32.8), 120 (53.3) |

4.6 g of this free base was dissolved in a small amount of acetone. The obtained solution was added to a saturated solution of 1.3 g of fumaric acid in acetone to precipitate a crystal. This crystal was filtered and recrystallized from ethanol to obtain 4.80 g of the corresponding monofumarate.

fumarate: mp 115 to 118° C.
NMR δ (d₆—DMSO): 1.35 (3H, t, J = 7.0 Hz; OCH₂C<u>H</u>₃), 1.92 (2H, m,;

—CH₂C<u>H</u>₂—), 2.50 (3H, s, —CH₃), 263 (3H, s; —CH₃), 2.6~2.75

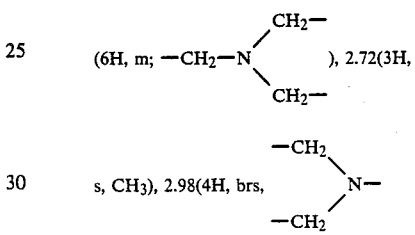

(6H, m; —CH₂—N(CH₂—/CH₂—)), 2.72(3H, s, CH₃), 2.98(4H, brs, 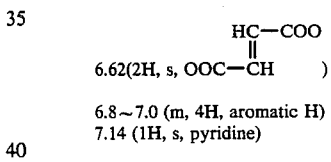 —CH₂\N—/—CH₂ phonyl)4.0(4H, m; —CON—CH₂— and —OC<u>H</u>₂CH₃), 6.62(2H, s, OOC—CH=CH—COO )

6.8~7.0 (m, 4H, aromatic H)
7.14 (1H, s, pyridine)

The following compounds were prepared in a similar manner as above.

| Compound No. | Mass m/z (relative intensity): | Monofumarate mp |
|---|---|---|
| 7 | 449 (M⁺, 67.0), 219 (57.1), 190 (44.4), 189 (51.2), 148 (31.9), 134 (64.8), 106 (37.6) | 118~120° C. (MeOH—acetone) |
| 8 | 421 (M⁺, 16.4), 220 (16.6), 219 (100), 176 (18.6), 120 (23.7) | hemi-fumarate 160.5~162° C. (EtOH) |
| 3 | 392 (M⁺, 20.3), 219 (100), 205 (18.4) | 177~180° (EtOH) |
| 4 | 405 (M⁺, 100), 230 (57.3), 219 (80.), 201 (56.7) | 169~173° C. (EtOH) |

EXAMPLE 3

3-Phenyl-5,7-dimethyl-1-[4-[4-(2-ethoxyphenyl)-1-piperazinyl]butyl]pyrido[2,3-d]pyrimidine-2,4(1H,3H)-dione monofumarate (Compound No. 10)

(1) Synthesis of 3-phenyl-5,7-dimethyl-1-(4-bromobutyl)pyrido[2,3-d]pyrimidine-2,4(1H,3H)-dione A mixture comprising of 13.36 g 3-phenyl-5,7-dimethylpyrido[2,3-d]pyrimidine-2,4(1H,3H)-dione, 43.18 g of 1,4-dibromobutane, 10.37 g of anhydrous potassium carbonate and 150 ml of N,N-dimethyl-formamide was heated at 80° C. for 3 hours. After the completion of the reaction, the reaction mixture was poured into 600 ml of water. The resulting mixture was extracted with ethyl acetate and further with a small amount of dichloromethane. These extracts were combined, dried over anhydrous potassium carbonate and distilled under a reduced pressure to remove the solvent. The obtained residue was dissolved in a small amount of dichloromethane, columnchromatographed over silica gel column and eluted with dichloromethane. The eluate was concentrated under a reduced pressure and the residue was recrystallized from a dichloromethaneisopropyl ether solvent to give 13.06 g of 3-phenyl-5,7-dimethyl-1-(4-bromobutyl)pyrido[2,3-d]-pyrimidin-2,4(1H,3H)-dione having a melting point of 153.5° to 154.5° C., which serves as an intermediate (yield: 65%).

(2) 3-Phenyl-5,7-dimethyl-1-[4-[4-(2-ethoxyphenyl)-1-piperazinyl]butyl]pyrido[2,3-d]pyrimidine-2,4(1H,3H)-dione monofumarate 4.02 g of 3-phenyl-5,7-dimethyl-1-(4-bromobutyl)-pyrido[2,3-d]pyrimidine-2,4(1H,3H)-dione prepared in the step (1), 3.64 g of 1-(2-ethoxyphenyl)piperazine and 4.2 ml of triethylamine were added to 30 ml of ethanol. The mixture was heated under reflux for 3 hours. After the completion of the reaction, the reaction mixture was concentrated under a reduced pressure. Water was added to the residue. The resulting mixture was extracted with dicoloromethane. The organic layer was dried over anhydrous potassium carbonate and distilled under a reduced pressure to remove the solvent. The residue was recrystallized from an ethyl acetatedichloromethane solvent to give 4.56 g of the objective compound having a melting point of 149° to 151° C. (yield: 86.5%).

---

Mass m/z (relative intensity): 527 (M$^+$, 60.2), 352 (11.6), 268 (12.6), 219 (100), 204 (15.2), 191 (13.2), 120 (14.4)

---

3.96 g of the obtained free base was dissolved in acetone. According to an ordinary process, a solution of 0.87 g of fumaric acid in acetone was added to the obtained solution to precipitate a crystal. The crystal was filtered and recrystallized from a methanol-acetone solvent to give 3.85 g of the corresponding monofumarate having a melting point of 170° to 175° C. ( dec.).

NMR δ (CD$_3$OD): 1.42 (3H, t; J = 7.0 Hz; OCH$_2$C<u>H</u>$_3$), 1.8~2.0 (4H, m, =

NC<u>H</u>$_2$C<u>H</u>$_2$CH$_2$CH$_2$N=)

2.56 (3H, s; CH$_3$); 2.71(3H, s; CH$_3$)

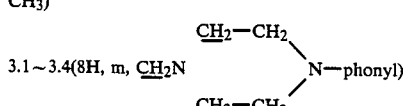

3.1~3.4(8H, m, C<u>H</u>$_2$N

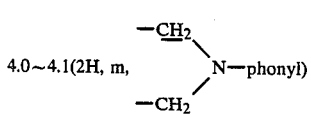

4.0~4.1(2H, m, 4.4~4.5(2H, t, J = 7.0Hz; —CO—NCH$_2$—)

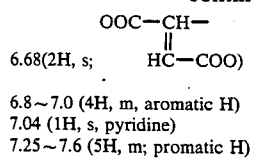

6.68(2H, s;

6.8~7.0 (4H, m, aromatic H)
7.04 (1H, s, pyridine)
7.25~7.6 (5H, m; promatic H)

The following compound was prepared in a similar manner as above.

| Compound No. | Mass (relative intensity) | Free acid | Monofumarate mp |
|---|---|---|---|
| 9 | 407 (M$^+$, 36.5), 219 (100), 204 (19.2), 176 (28.8), 134 (21.3), 120 (31.7) | ( dichloromethane AcOEt ) | 181~183.5° C. (EtOH) |

EXAMPLE 4

3-Phenyl-5,7-dimethyl-1-[2-[4-(2-ethoxyphenyl)-1-piperazinyl]ethyl]pyrido[2,3-d]pyrimidin-2,4(1H,3H)-dione monofumarate (Compound No. 11)

2.67 g of 3-phenyl-5,7-dimethyl-pyrido[2,3-d]-pyrimidine-2,4(1H,3H)-dione, 4.03 g of 4-(2-ethoxyphenyl)-1-(2-chloroethyl)piperazine and 2.76 g of anhydrous potassium carbonate were added to 30 ml of dimethylformamide. The obtained mixture was heated at 80° C. for 3 hours. After the completion of the reaction, the reaction mixture was concentrated under a reduced pressure. Water and dichloromethane were added to the obtained residue and the resulting mixture was extracted with dichloromethane. The organic layer was dried over anhydrous potassium carbonate and distilled under a reduced pressure to remove the solvent. The residue was columnchromatographed over silica gel column and eluted with a dichloromethane-ethyl acetate solvent (1:1). The eluent was concentrated under a reduced pressure and the residue was recrystallized from a dichloromethane-ethyl acetate solvent to give 3.27 g of the objective compound having a melting point of 182° to 183° C. (yield: 65.5%).

---

Mass m/z (relative intensity): 499 (M$^+$, 31.0), 294 (90.2), 232 (42.2), 219 (100), 204 (35.3), 176 (52.4), 161 (19.8).

---

This free base was converted into the corresponding monofumarate according to an ordinary process. m.p.: 185° to 187° C. (dec.) (MeOH)

NMR δ (d$_6$—DMSO): 1.34(3H, t, J = 7.0 Hz; OCH$_2$C<u>H</u>$_3$)

2.53(3H,; CH$_3$),2.65(3H,s; CH$_3$),

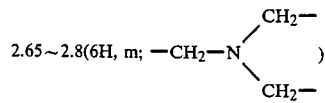

2.65~2.8(6H, m; —CH$_2$—N

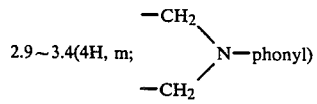

2.9~3.4(4H, m;

-continued 3.98(2H, q, J = 7.0Hz; —OC$\underline{H}_2$CH$_3$)

4.42(2H, t, J = 7.0Hz, —CON—CH$_2$—)

6.59(2H, s; OOC—CH=HC—COO)

6.8~6.95(4H, m; aromatic H)
7.07(1H, s; pyridine H)
7.2~7.5(5H, m; aromatic H)

EXAMPLE 5

(1) 3-{4-[4-(2-Ethoxyphenyl)-1-piperazinyl]butyl}-4(3H)-quinazolone (Compound No. 5) difumarate A mixture comprising 1.63 g of 2H-3,1-benzoxazine-2,4(1H)-dione, 1.78 g of ethyl orthoformate and 2.77 g of 4-(2-ethoxyphenyl)-1-(4-aminobutyl)piperazine was heated on a boiling water bath for about 10 minutes and further heated on an oil bath of 120° to 130° C. for about 2 hours. After the completion of the reaction, the reaction mixture was concentrated under a reduced pressure and the residue was columnchromatographed over silica gel column and eluted with an ethyl acetatetriethylamine solvent (30:1) to give 1.5 g of 3-{4-[4-(2-ethoxyphenyl)-1-piperazinyl]butyl}-4(3H)-quinazolone as an oil (yield: 66.7%).

NMR δ (CDCL$_3$): 1.42(3H,t, J = 7.0 Hz;
—CH$_2$C$\underline{H}_3$), 1.0~2.1(4H, m; —NCH$_2$C$\underline{H}_2$C$\underline{H}_2$CH$_2$N—), 2.2~2.8(6H, m; —CH$_2$\\N—CH$_2$—/—CH$_2$)

2.9~3.3(4H, m, —CH$_2$\\N—phenyl)/—CH$_2$)

3.7~4.3(4H, m, —CON—CH$_2$— and —OC$\underline{H}_2$CH$_3$)

6.85 (4H, br s, aromatic H)
7.15 ~ 7.9 (3H, m, aromatic H)
8.0 (1H,s,C$_2$—H)
8.30 (1H,d,J = 7.5 Hz, C$_5$—H)
m/z (relative intensity): 407 (M$^+$ + 1, 27.9),
406 (M$^+$, 100.0), 219 (89.9), 204 (20.3),
150 (26.4), 146 (21.1), 120 (41.6)

1.50 g of this oily free base was dissolved in a small amount of acetone. The obtained solution was added to a saturated solution of 0.857 g of fumaric acid in acetone to precipitate a crude crystal. The crude crystal was recrystallized from ethanol to give 1.65 g of the corresponding monofumarate having a melting point of 197° to 198° C. as a colorless prisms.

What is claimed is:

1. A phenylpiperazine derivative represented by the formula:

[Structure: 2-OR$_1$-phenyl-piperazine-N—(CH$_2$)$_n$—R$_2$]

wherein R$_1$ stands for an ethyl group; R$_2$ stands for a group represented by the formula:

[Structure showing quinazolone-type ring with R$_5$, R$_4$, Y, R$_3$ substituents and carbonyl]

(wherein R$_3$, R$_4$ and R$_5$ each stand for a hydrogen atom or a methyl group and Y stands for CH); and n stands for an integer of 2 or 4, and pharmaceutically acceptable acid solution salts thereof.

2. A phenylpiperazine derivative and pharmaceutically acceptable acid addition salts thereof as set forth in claim 1, wherein said derivative represented by the formula [1] is 3-[2-[4-(2-ethoxyphenyl)-1-piperazinyl]ethyl]-4(3H)-quinazolone.

3. A phenylpiperazine derivative and pharmaceutically acceptable acid addition salts thereof as set forth in claim 1, wherein said derivative represented by the formula [1] is 3-[4-[4-(2-ethoxyphenyl)-1-piperazinyl]butyl]-4(3H)-quinazolone.

* * * * *